US012661047B2

(12) United States Patent
Damaser et al.

(10) Patent No.: US 12,661,047 B2
(45) Date of Patent: Jun. 23, 2026

(54) DETRUSOR PRESSURE ESTIMATION FROM SINGLE CHANNEL BLADDER PRESSURE RECORDINGS

(71) Applicants: THE CLEVELAND CLINIC FOUNDATION, Cleveland, OH (US); The United States Government as represented by the Department of Veterans Affairs, Washington, DC (US)

(72) Inventors: Margot S. Damaser, Cleveland Heights, OH (US); Steve Majerus, Cleveland Heights, OH (US); Mohamed Abdelhady, Cleveland, OH (US)

(73) Assignees: THE CLEVELAND CLINIC FOUNDATION, Cleveland, OH (US); THE DEPARTMENT OF VETERANS AFFAIRS, Washington, DC (US)

( * ) Notice: Subject to any disclaimer, the term of this patent is extended or adjusted under 35 U.S.C. 154(b) by 995 days.

(21) Appl. No.: 17/880,109

(22) Filed: Aug. 3, 2022

(65) Prior Publication Data

US 2023/0041528 A1 Feb. 9, 2023

Related U.S. Application Data

(60) Provisional application No. 63/340,842, filed on May 11, 2022, provisional application No. 63/228,672, filed on Aug. 3, 2021.

(51) Int. Cl.
*A61B 5/20* (2006.01)
*A61B 5/00* (2006.01)

(52) U.S. Cl.
CPC ............ *A61B 5/205* (2013.01); *A61B 5/6852* (2013.01); *A61B 5/7203* (2013.01); *A61B 5/726* (2013.01)

(58) Field of Classification Search
CPC ......... A61B 5/205; A61B 5/076; A61B 5/202; A61B 5/6874; A61B 5/721; A61B 5/726;
(Continued)

(56) References Cited

U.S. PATENT DOCUMENTS

2007/0255090 A1 11/2007 Addington et al.
2016/0354028 A1 12/2016 Damaser et al.
(Continued)

FOREIGN PATENT DOCUMENTS

WO WO-2008130467 A1 * 10/2008 ............. A61B 5/204
WO WO-2018075468 A1 * 4/2018 .......... A61B 5/6874
WO WO-2025076375 A1 * 4/2025 .......... A61B 5/6853

OTHER PUBLICATIONS

Klunder M, Sawodny O, Amend B, Ederer M, Kelp A, Sievert KD, Stenzl A, Feuer R. Signal processing in urodynamics: towards high definition urethral pressure profilometry. Biomed Eng Online. Mar. 22, 2016;15:31. doi: 10.1186/s12938-016-0145-6. PMID: 27000558; PMCID: PMC4802619.

(Continued)

*Primary Examiner* — Brian L Casler
(74) *Attorney, Agent, or Firm* — Tarolli, Sundheim, Covell & Tummino LLP

(57) ABSTRACT

To perform urological diagnostics of a patient, detrusor pressure can be estimated using bladder pressure recordings from a single sensor. A signal comprising the bladder pressure data recorded by the sensor can be received. The bladder pressure data can include at least a detrusor pressure data component and a corrupting data component. An estimate of the corrupting data component can be extracted from the bladder pressure data. The detrusor pressure of the patient can be estimated based on the estimate of the corrupting data component and/or the estimate of the detrusor pressure data. An output indicative of the detrusor
(Continued)

pressure of the patient can be provided based on the estimate
of the detrusor pressure data component.

9 Claims, 5 Drawing Sheets

(58) Field of Classification Search
CPC ....... A61B 5/7282; A61B 5/0031; A61B 5/03;
A61B 2560/0214; A61B 2560/0219;
A61B 2562/0247; A61B 5/6852; A61B
5/7203; A61B 5/036; A61N 1/36007;
A61N 1/3606; A61N 1/36135; A61N
1/36167
USPC ........................... 600/29, 300, 561, 587, 562
See application file for complete search history.

(56) References Cited

U.S. PATENT DOCUMENTS

| | | | |
|---|---|---|---|
| 2019/0216401 A1* | 7/2019 | Brody ............. | A61M 25/10185 |
| 2019/0223775 A1 | 7/2019 | Damaser et al. | |
| 2020/0405467 A1 | 12/2020 | Dhar et al. | |

OTHER PUBLICATIONS

Karam, Robert; Case Western Reserve University School of Graduate Studies thesis of Robert Karam candidate for the degree of Master of Science, Dated Jul. 24, 2015, pp. 1-53.

PCT Search Report for Corresponding Application Serial No. PCT/US2022/039270, Dated Nov. 21, 2022, pp. 1-27.

EP Rule 161 Communication for European Patent Application No. 22761751.1, dated Mar. 19, 2024, 3 pgs.

\* cited by examiner

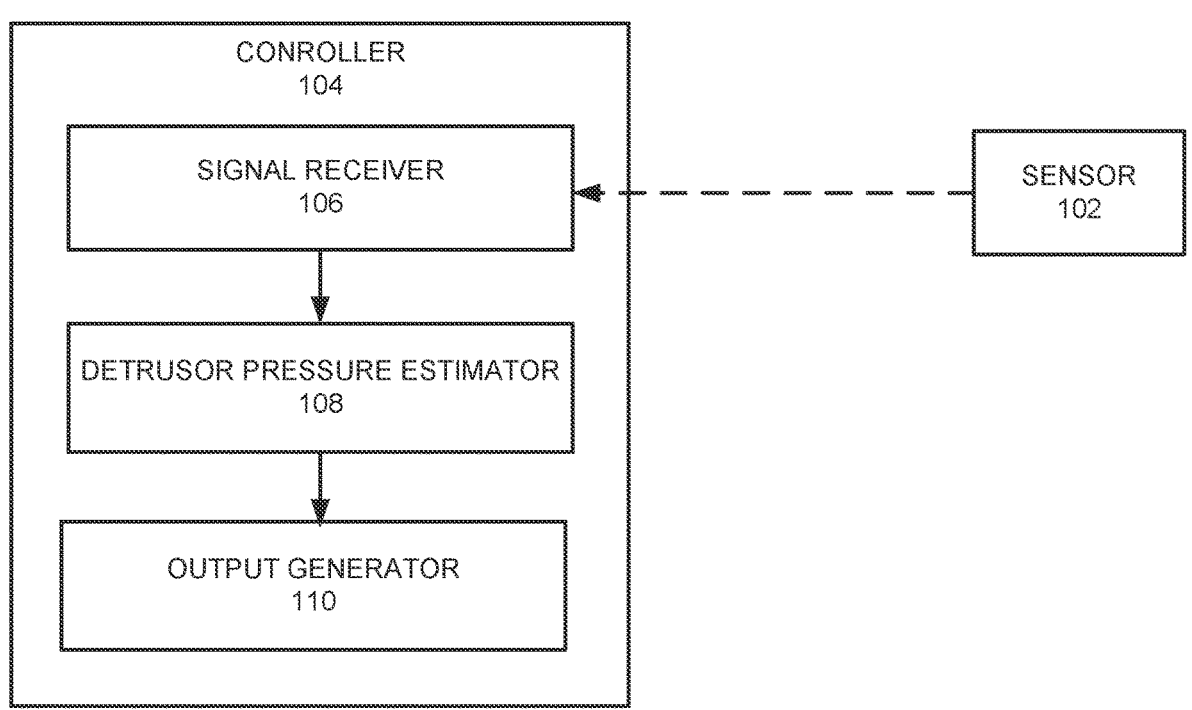
FIG. 1

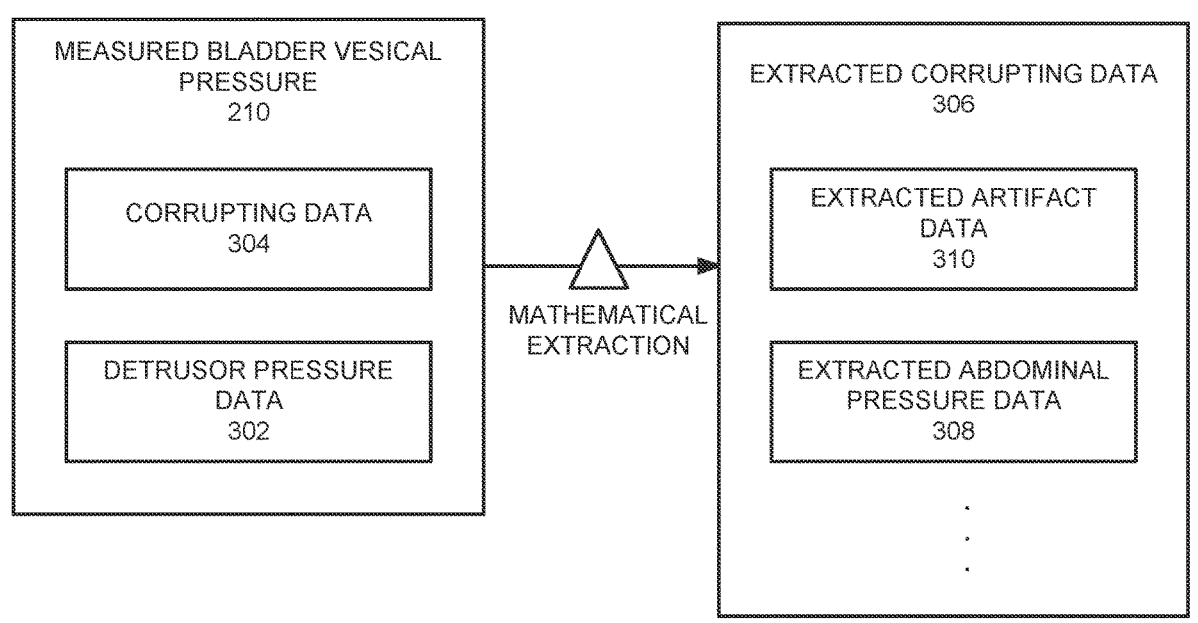
FIG. 3

400

```
┌─────────────────────────┐
│ MEASURED BLADDER VESICAL│
│        PRESSURE         │
│           210           │
└─────────────────────────┘
            │
            ▼
           (⊕) ──────────────────────►  ┌───────────────────────────────┐
            ▲                            │ ESTIMATED DETRUSOR PRESSURE   │
            │                            │             402               │
            │                            └───────────────────────────────┘
┌─────────────────────────────────┐
│  EXTRACTED CORRUPTING DATA      │
│             306                 │
│   ┌───────────────────────┐     │
│   │     EXTRACTED         │     │
│   │   ARTIFACT DATA       │     │
│   │        310            │     │
│   └───────────────────────┘     │
│   ┌───────────────────────┐     │
│   │     EXTRACTED         │     │
│   │    ABDOMINAL          │     │
│   │  PRESSURE DATA        │     │
│   │        308            │     │
│   └───────────────────────┘     │
│             .                   │
│             .                   │
│             .                   │
└─────────────────────────────────┘
```

FIG. 4

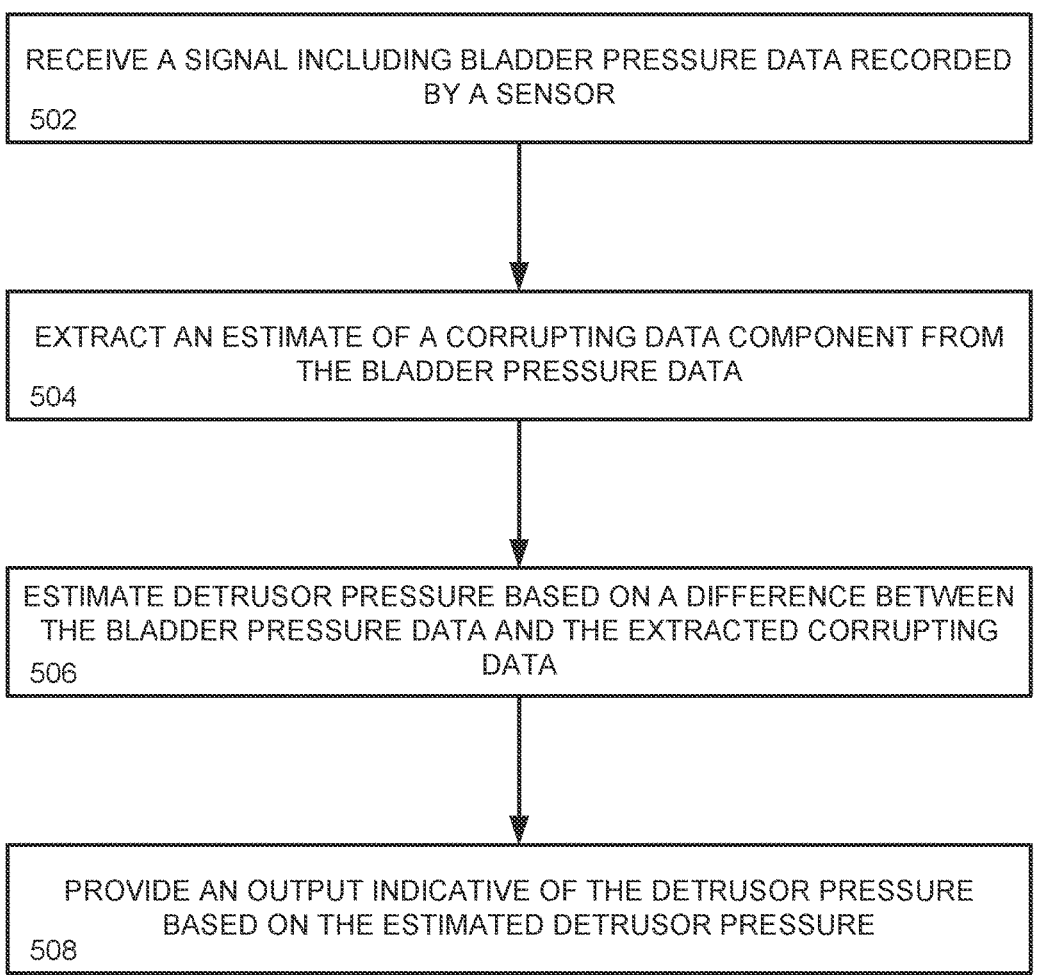
FIG. 5

DETRUSOR PRESSURE ESTIMATION FROM SINGLE CHANNEL BLADDER PRESSURE RECORDINGS

CROSS-REFERENCE TO RELATED APPLICATIONS

This application claims the benefit of U.S. Provisional Application Ser. No. 63/340,842, filed 11 May 2022, entitled "DETRUSOR PRESSURE ESTIMATION FROM SINGLE CHANNEL BLADDER PRESSURE RECORDINGS" and U.S. Provisional Application Ser. No. 63/228,672, filed 3 Aug. 2021, entitled "SINGLE CATHETER DETERMINATION OF DETRUSOR PRESSURE". The entirety of these applications is incorporated by reference for all purposes.

TECHNICAL FIELD

The present disclosure relates generally to urodynamics and, more specifically, to systems and methods for estimating detrusor pressure from bladder vesical pressure recorded by a single sensor.

BACKGROUND

Disorders of the lower urinary tract are often characterized by symptoms like increased urinary frequency, nocturia, urinary urgency, and urinary incontinence. Such disorders are typically diagnosed with a catheter-based urodynamic study. Traditionally, such catheter based urodynamic studies require monitoring bladder vesical pressure ($P_{VES}$) using a first catheter placed within the bladder and measuring abdominal pressure ($P_{ABD}$) using a second catheter placed elsewhere (e.g., the rectum). Both $P_{VES}$ and $P_{ABD}$ measurements are required in order to distinguish pressure changes arising uniquely from the detrusor ($P_{DET}$), which is not uniquely measurable. A given assumption in such urodynamics studies is that all changes in $P_{ABD}$ are reflected within $P_{VES}$ and therefore $P_{DET}$ can be determined by linear subtraction of $P_{ABD}$ from $P_{VES}$ ($P_{DET}=P_{VES}-P_{ABD}$). However, using two catheters for urodynamics studies is bulky and uncomfortable for the patient. Moreover, the use of two catheters increases the possibility of inaccurate results if one of the catheters slips from proper positioning.

SUMMARY

In an advance over traditional urodynamic studies that require two catheters, the present disclosure relates to estimating detrusor pressure ($P_{DET}$) requiring measurement of only bladder vesical pressure ($P_{VES}$) recordings from a single sensor. Corrupting data ($P_{CORR}$) can be mathematically extracted from $P_{VES}$ and subsequently subtracted from $P_{VES}$ to determine $P_{DET}$. The ability to detect $P_{DET}$ using only $P_{VES}$ pressure recordings from a single sensor within the bladder would simplify urodynamics by eliminating the need for a separate catheter (e.g., in the rectum) to measure $P_{ABD}$ and/or could improve abdominal pressure artifact rejection in standard urodynamics.

In an aspect, the present disclosure includes a system configured for urological diagnostics of a patient. The system may include a sensor configured to detect bladder vesical pressure data. The bladder vesical pressure data can include at least a detrusor pressure data component and a corrupting data component. A controller can be coupled to the sensor and may include at least a processor configured to: receive a signal comprising the bladder vesical pressure data from the sensor; extract an estimate of the corrupting data component from the bladder vesical pressure data; estimate the detrusor pressure of the patient based on the estimate of the corrupting data component; and provide an output indicative of the detrusor pressure of the patient based on the estimate of the detrusor pressure data component.

In another aspect, the present disclosure includes a method for urological diagnostics of a patient. The method can be performed by a controller that includes a processor. A signal comprising bladder pressure data recorded by a sensor can be received by the controller. The bladder pressure data can include at least a detrusor pressure data component and a corrupting data component. An estimate of the corrupting data component can be extracted from the bladder pressure data by the controller. The detrusor pressure of the patient can be estimated by the controller based on the estimate of the corrupting data component and/or the estimate of the detrusor pressure data. The controller can provide an output indicative of the detrusor pressure of the patient based on the estimate of the detrusor pressure data component.

BRIEF DESCRIPTION OF THE DRAWINGS

The foregoing and other features of the present disclosure will become apparent to those skilled in the art to which the present disclosure relates upon reading the following description with reference to the accompanying drawings, in which:

FIG. 1 is an illustration of a system that can perform urological diagnostics of a patient by estimating detrusor pressure from bladder vesical pressure recorded by a single sensor;

FIGS. 2-4 are illustrations of how the system of FIG. 1 can estimate the detrusor pressure; and FIG. 5 is a process flow diagram of a method for performing urological diagnostics of a patient by estimating detrusor pressure from bladder vesical pressure recorded by a single sensor.

DETAILED DESCRIPTION

I. Definitions

Figure 2:
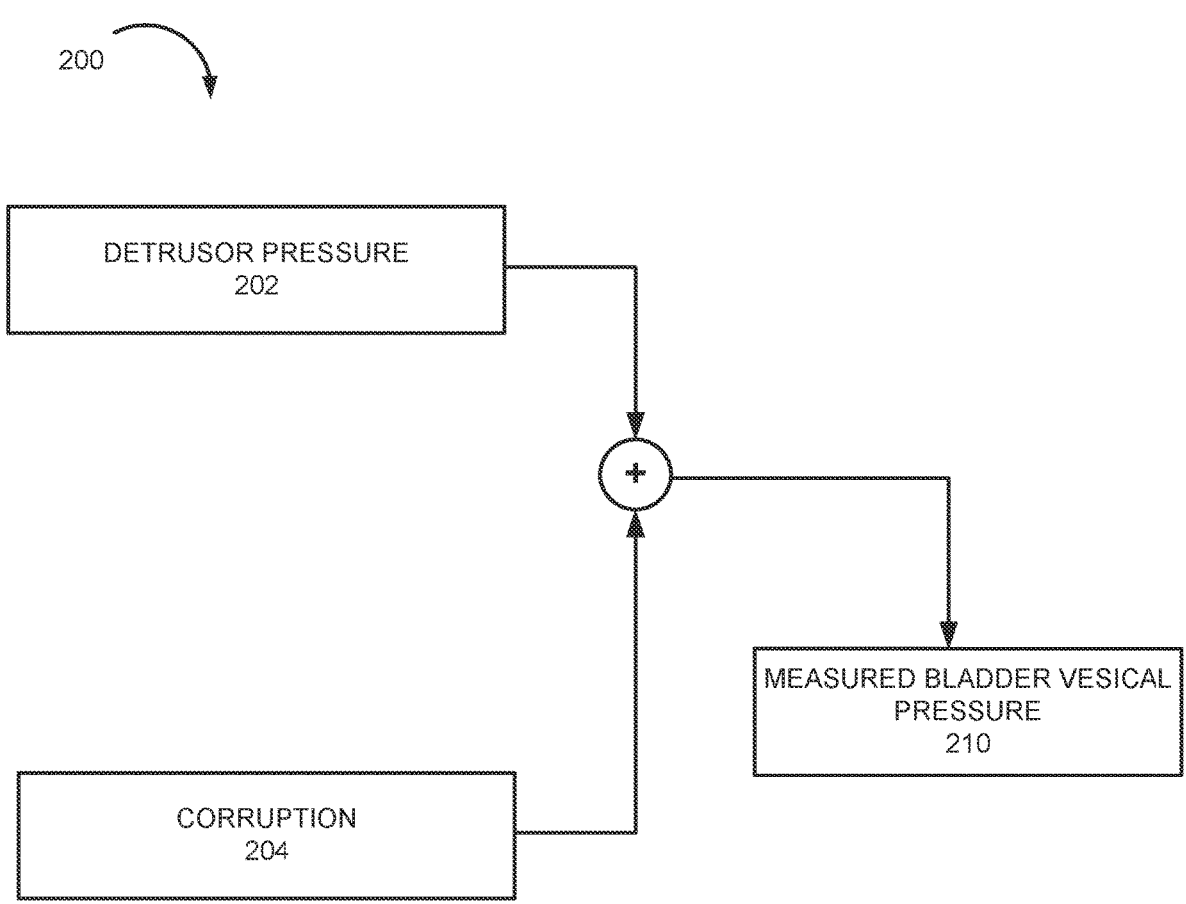

In the context of the present disclosure, the singular forms "a," "an" and "the" can also include the plural forms, unless the context clearly indicates otherwise.

The terms "comprises" and/or "comprising," as used herein, can specify the presence of stated features, steps, operations, elements, and/or components, but do not preclude the presence or addition of one or more other features, steps, operations, elements, components, and/or groups.

As used herein, the term "and/or" can include any and all combinations of one or more of the associated listed items.

Additionally, although the terms "first," "second," etc. may be used herein to describe various elements, these elements should not be limited by these terms. These terms are only used to distinguish one element from another. Thus, a "first" element discussed below could also be termed a "second" element without departing from the teachings of the present disclosure. The sequence of operations (or acts/steps) is not limited to the order presented in the claims or figures unless specifically indicated otherwise.

As used herein, the term "urodynamics" refers to the science behind a diagnostic urodynamic study that tests how well the lower urinary tract (e.g., bladder, sphincters, and urethra) hold and release urine. For example, such urodynamic tests can show how well the bladder works and why leaks and/or blockages occur.

As used herein, the term "bladder" can refer to the "urinary bladder", a hollow organ that collects urine before disposal by urination.

As used herein, the term "bladder vesical pressure" or "$P_{VES}$", also referred to as "bladder pressure" refers to the pressure within the bladder that can be recorded by a sensor within the bladder. The recorded data is referred to as bladder pressure data or bladder vesical pressure data.

As used herein, the term "abdominal pressure" or "$P_{ABD}$", refers to the pressure applied to the bladder via the abdominal muscles. Measurement obtained from a catheter not within the bladder (e.g., a rectal catheter) during a urodynamic study can be referred to as abdominal pressure data.

As used herein, the term "detrusor" generally refers to a smooth muscle that forms a layer of the wall of the bladder. The detrusor muscle generally facilitates contraction of the bladder wall during micturition (also referred to as urination).

As used herein, the term "detrusor pressure" or "$P_{DET}$", refers to pressure changes arising uniquely from the change in force of the detrusor. Detrusor pressure is considered the true bladder pressure but is not directly measurable. In traditional urodynamic studies, an estimated detrusor pressure data component can be found by subtracting abdominal pressure data ($P_{ABD}$), which is recorded by a sensor in a catheter not positioned within the bladder (e.g., a rectal catheter), from the bladder vesical pressure data ($P_{VES}$), which is recorded by a sensor within the bladder. However, as described herein, the $P_{DET}$ can be estimated with only measurements from a single sensor in the bladder by subtracting a mathematically discovered corrupting data component ($P_{CORR}$) from the bladder vesical pressure data ($P_{VES}$) recorded by the single sensor within the bladder.

As used herein, the term "corrupting data component" refers to one or more components of the bladder vesical pressure (e.g., abdominal pressure, artifacts, or the like) that cause the bladder vesical pressure to differ from the detrusor pressure data during urodynamics studies. Detrusor pressure data can be determined by subtracting the corrupting data components ($P_{CORR}$) from the bladder vesical pressure data ($P_{VES}$).

As used herein, the term "patient" refers to any warm-blooded organism (e.g., a human being, a primate, a cat, a dog, a rabbit, a mouse, etc.). Other terms, like subject, can be used interchangeably with the term patient.

As used herein, the term "real-time" can refer to a time during which an event or process occurs. For example, something referred to as real-time can occur within 1000 milliseconds or less from when the event or processor occurs.

II. Overview

It is well known in the field of urodynamics that detrusor pressure ($P_{DET}$) is not uniquely measurable. Currently, a patient's $P_{DET}$ can be estimated by taking bladder vesical pressure ($P_{VES}$), measured using a first catheter placed within the bladder, and subtracting abdominal pressure ($P_{ABD}$), measured using a second catheter placed elsewhere (e.g., the rectum). Using the commonly accepted assumption that all changes in $P_{ABD}$ are reflected within $P_{VES}$, the linear subtraction of $P_{ABD}$ from $P_{VES}$ can be used to distinguish pressure changes arising uniquely from the detrusor ($P_{DET}$). However, using two catheters to estimate $P_{DET}$ is not only bulky and uncomfortable for the patient, but also may not give an inaccurate result (e.g., due to extra recording, inaccurate positioning, or the like).

Using a single catheter or an ambulatory urodynamics sensor within a patient's bladder is far more comfortable and less bulky for the patient, uses fewer disposable catheters, and also will introduce less error into calculations. Accordingly, in an advance over traditional urodynamic studies, the present disclosure relates to estimating detrusor pressure ($P_{DET}$) using bladder vesical pressure ($P_{VES}$) recordings from a single sensor in the bladder (without requiring an extra sensor to record abdominal pressure) and subtracting corrupting data ($P_{CORR}$), which may account for abdominal pressure, artifact, and the like, from $P_{VES}$. The $P_{CORR}$ can be mathematically extracted from the $P_{VES}$ in real time. The ability to detect $P_{DET}$ using a single $P_{VES}$ pressure recorded by a single sensor would simplify urodynamics by eliminating the need for a separate catheter to measure $P_{ABD}$ or could improve abdominal pressure artifact rejection in standard urodynamics. Alternatively, in some instances, when the abdominal pressure may be useful (e.g., in patients who generate bladder emptying using mainly abdominal pressure) the $P_{CORR}$ that has been estimated and extracted can be displayed as a measure of $P_{ABD}$ (this works because $P_{ABD}$ is a major contributor to $P_{CORR}$). In other instances, $P_{ABD}$ may be further mathematically determined from the $P_{CORR}$ estimate.

III. Systems

Detrusor pressure ($P_{DET}$), which can be used in many urological diagnostic applications, is not independently detectable. Accordingly, the traditional way to determine $P_{DET}$ is by using two separate sensors (e.g., catheters), one within the bladder to detect bladder vesical pressure ($P_{VES}$) and another catheter in another location (e.g., the rectum) to detect abdominal pressure ($P_{ABD}$). Both $P_{VES}$ and $P_{ABD}$ are assumed to reflect all the abdominal pressure of a patient such that $P_{DET}=P_{VES}-P_{ABD}$. However, $P_{ABD}$ does not always accurately reflect all of the abdominal pressure of the patient because the second catheter can add noise artifacts into recordings and errors due to improperly maintained positioning. Moreover, the second catheter is traditionally positioned in the rectum and many patients do not want a rectal catheter.

Advantageously, the system 100 (FIG. 1) can estimate $P_{DET}$ from only $P_{VES}$. In other words, the system 100 only requires a single sensing device and/or catheter (e.g., a catheter having one or more sensors that travels through the patient's urethra until at least one of the one or more sensors is within the patient's bladder or an ambulatory urodynamics device having at least one sensor) (shown generically as sensor 102) within the patient's bladder to record $P_{VES}$. $P_{DET}$ can then be estimated from just the measurement of $P_{VES}$ (from the sensor 102). The $P_{VES}$ recordings can include both a detrusor pressure component $P_{DET}$ and a corrupting data component $P_{CORR}$. The corrupting data ($P_{CORR}$) can be mathematically extracted from $P_{VES}$ and subsequently subtracted from $P_{VES}$ to determine $P_{DET}$ ($P_{DET}=P_{VES}-P_{CORR}$). $P_{CORR}$ may include abdominal pressure data, artifact data, and/or additional noise and/or error data. Extracting the $P_{CORR}$ from the $P_{VES}$ thereby allows for accurately and precisely estimating $P_{DET}$ without needing a second pressure (e.g., $P_{ABD}$) to be measured. In some instances, $P_{DET}$ can be estimated in real time (as the sensor 102 records the $P_{VES}$ data). Such real time estimation can allow the person doing the test to identify and/or further investigate specific features/results of the $P_{DET}$ estimates that seem abnormal and/or unexpected during a single test session. For example, the person administering the urodynamics test can notice that the $P_{VES}$ recordings are inaccurate and then investigate the cause for the $P_{VES}$ recordings being inaccurate and fix the cause before continuing with the test. In this sense, the system 100 can reduce the time required to diagnose conditions evident from $P_{DET}$ and can require less effort and experience to perform the diagnostics. System 100 can also reduce the pain and discomfort of the patient during the testing process and require less repeat testing. The converse to this relationship ($P_{DET}=P_{VES}-P_{CORR}$) is that if $P_{DET}$ is estimated, the remainder of the $P_{VES}$ is $P_{CORR}$, which may provide an approximation of the abdominal pressure ($P_{ABD}$) (because the major contributor to $P_{CORR}$ is $P_{ABD}$). $P_{ABD}$ can be an important measurement, for example in cases where a patient predominantly uses abdominal pressure to enable bladder voiding.

The system 100 can include a sensor 102 electrically coupled with and a controller 104. The sensor 102 can be positioned at least partially within the bladder of the patient to detect and record the $P_{VES}$ data. The sensor 102 can transmit the $P_{VES}$ data to the controller 104 (e.g., as the $P_{VES}$ data is recorded in the bladder or at a time after the data has been recorded) according to a wireless connection and/or a wired connection. For example, the sensor 102 can include a wireless transmitter, a wired transmitter, or the like. In some instances, the sensor 102 may also include non-transitory memory capability and may include a data processing capability.

As previously noted, the sensor 102 may be referred to herein as a single sensor. As used herein, the term "single" before sensor refers to one or more sensors that are within the bladder without requiring an extra one or more sensors (e.g., located within a different catheter) to record abdominal pressure. For example, the single sensor can be within a single catheter and/or a single ambulatory device (without requiring a second sensor in another location to record abdominal pressure ($P_{ABD}$). The single sensor can record $P_{VES}$ from a location within the bladder for a time period and send the recorded $P_{VES}$ to the controller 104, residing outside the bladder, for further analysis. Alternatively, the sensor 102 may be located outside of the bladder and coupled to bladder pressure via air or water as the transducing medium.

The controller 104 can be a computing device that includes at least a hardware processor or microprocessor. The processor or microprocessor may perform operations of a non-transitory memory. However, in some instances, the controller 104 can include a non-transitory memory. The non-transitory memory can store instructions related to determining an estimate of $P_{DET}$ from the recorded $P_{VES}$ and the processor can execute the instructions to determine an estimate of $P_{DET}$ from the recorded $P_{VES}$. The controller 104 can also include one or more transceivers (wired and/or wireless), as well as any other hardware or software required by the system 100.

As noted, the processor of controller 104 can access the non-transitory memory to execute the instructions to perform the acts of a signal receiver 106, a detrusor pressure estimator 108, and an output generator 110. The sensor 102 can send a signal including the recorded $P_{VES}$ data to the signal receiver 106 of the controller 104 and the signal receiver can receive the signal. The bladder vesical pressure ($P_{VES}$) data can include at least a detrusor pressure data component ($P_{DET}$) and a corrupting data component ($P_{CORR}$). The detrusor pressure estimator 108 can estimate $P_{DET}$ from the $P_{VES}$ data. The output generator 110 can generate an output indicative of the detrusor pressure based on the estimated $P_{DET}$, which can be used for diagnostic purposes. The output can be provided by the output generator 110 contemporaneously to the sensor 102 detecting the bladder vesical pressure data. Additionally, the processor of the controller 104 can account for a variable relationship between the detrusor pressure data component and the corrupting data component as the bladder empties or fills.

The detrusor pressure estimator 108 can employ the steps shown in FIGS. 2-4 to mathematically extract an estimate of the corrupting data component ($P_{CORR}$) from the recorded bladder vesical pressure ($P_{VES}$) data and subsequently estimate the detrusor pressure ($P_{DET\_EST}$) of the patient based on a difference between the estimate of the $P_{CORR}$ and the $P_{VES}$ data. As shown in FIG. 2, the detrusor pressure 202 ($P_{DET}$) and corrupting data 204 ($P_{CORR}$) combine to form the measured bladder vesical pressure 210 ($P_{VES}$). In other words, the measurement of the bladder vesical pressure 210 ($P_{VES}$) at any given time includes the effects of the contraction of the detrusor muscle, the effects of abdominal muscle contraction, and noise and/or artifacts from the sensor itself. FIG. 3 shows the mathematical extraction of the extracted corrupting data 306 ($P_{CORREXT}$) from the bladder vesical pressure 210 ($P_{VES}$).

As discussed above the measured bladder vesical pressure 210 can include a corrupting data component 304 and the detrusor pressure data component 302. The extracted corrupting data 206 ($P_{CORREXT}$) is an estimate of the corrupting data component that is based on one or more mathematical transforms of the bladder vesical pressure data 210. The mathematical extraction can be performed using one or more mathematical transforms of at least a portion of data related to the measured bladder vesical pressure 210 ($P_{VES}$), for example, according to a time varying transform and/or a time-invariant transform. For example, at least one time-varying extraction technique may be a non-linear transform and/or a non-time-invariant transform. Examples of the time-varying operation used in the time-varying extraction technique include dynamic time warping approaches, autoregressive modeling such as linear predictive coding, discrete wavelet transform, or the like. The extracted corrupting data 206 ($P_{COREXT}$) can include, but is not limited to, extracted abdominal pressure data 308 and extracted artifact data 310 (as well as additional corrupting data in some instances), such that different transforms may be used to extract the abdominal pressure data 308 and the extracted artifact data 310.

As an example, the bladder vesical pressure data can be wavelet transformed and the wavelet transformed bladder vesical pressure data can include both detail coefficients and approximation coefficients. The wavelet transformed bladder vesical pressure data can include detail coefficients and approximation coefficients. The detail coefficients can relate to the corrupting data component and the approximation coefficients can relate to the detrusor pressure data component. The extraction can include filtering the detail coefficients related to the corrupting data component. There is high correlation at low-frequency between $P_{VES}$ and $P_{DET}$ in cystometry (a clinical diagnostic procedure used to evaluate bladder function that specifically measures contractile force of the bladder when voiding) and during bladder filling. Likewise, there is high correlation at high-frequency between $P_{VES}$ and $P_{ABD}$ in cystometry and during natural bladder filling. Additionally, noise artifacts have a different frequency than $P_{DET}$ and can be filtered either as part of the corrupting data and/or separately. As such the abdominal pressure component and the noise artifacts (e.g., from the sensor) of the measured bladder vesical pressure can be distinguished and extracted.

For example, the time-varying transform can account for temporal behaviors of the bladder pressure. As another example, the temporal behaviors of the bladder pressure may vary with the filling of the bladder (e.g., empty, 25% full, 50% full, 75% full, or 100% full, etc.). The time-varying extraction can account for how different levels of a bladder fullness (e.g., time-varying bladder volume) can affect the measured bladder vesical pressure because the relationship between detrusor and abdominal pressure might change as the bladder fills since the bladder filling displaces some abdominal volume and may change the transmission of abdominal pressures into the bladder. The time-varying bladder volume can be used as a control signal as the bladder fills.

FIG. 4 shows the estimation of the detrusor pressure 402 ($P_{DETEST}$). The extracted corrupting data 203 ($P_{CORREXT}$) (which is an estimate of the corrupting data component) can be subtracted from the measured bladder vesical pressure 210 ($P_{VES}$) to get the estimated detrusor pressure 402. The extracted corrupting data 306 ($P_{CORREXT}$) includes at least abdominal pressure data 308 and artifact data 310 that were extracted from the measured bladder vesical pressure 210 ($P_{VES}$). Thus, the influences of the corrupting signal components are removed and estimated detrusor pressure 402 ($P_{DETEST}$) can be determined and then output to the person in charge of the urodynamic diagnostic. The output can be provided in real time (e.g., as or a few seconds after the bladder pressure is recorded). A diagnosis of the patient can be made (and/or a potential diagnosis eliminated) based on the output. The output can be visually displayed on a display device (e.g., a computer monitor, a mobile device, etc.) in communication with the processor. The output can be displayed, for example, with one or more of a graphical representation, as data points relative to time, or the like.

IV. Methods

Another aspect of the present disclosure can include a method 500 (FIG. 5) for performing urological diagnostics of a patient by estimating detrusor pressure from bladder pressure recorded by a single sensor (for example, the method can be executed by a computing device, like controller 104, and receive data from sensor 102 of FIG. 1). For example, the single sensor can refer to one or more sensors that are located within the patient's bladder. For example, the single sensor can be on and/or within a bladder catheter (e.g., the bladder catheter can enter the body and travel through the patient's urethra until at least the sensor is within the bladder), on or within an ambulatory urodynamics sensor within a patient's bladder (e.g., the sensor can be floating within the bladder, against a wall of the bladder, etc.), or the like. Alternatively, the sensor may be located outside of the bladder, but coupled to bladder pressure via air or water as the transducing medium. Steps of the method 500 can be executed by a controller (e.g., similar to controller 104) that can act as a computing device that includes at least a processor or microprocessor and can perform operations of a non-transitory memory or can include a non-transitory memory.

The method 500 is illustrated as a process flow diagram with flowchart illustrations. For purposes of simplicity, the method 500 is shown and described as being executed serially; however, it is to be understood and appreciated that the present disclosure is not limited by the illustrated order as some steps could occur in different orders and/or concurrently with other steps shown and described herein. Moreover, not all illustrated aspects may be required to implement the method 400.

At Step 502, a signal comprising bladder pressure data recorded by the single sensor within the bladder can be received (e.g., by the controller 104). The bladder pressure (e.g., measured bladder vesical pressure 210) can include detrusor pressure (e.g., detrusor pressure 202) and corruption (e.g., corruption 204). In fact, the bladder pressure (e.g., measured bladder vesical pressure 210) can include detrusor pressure data (e.g., detrusor pressure data 302) and corrupting data (e.g., corrupting data 304).

At 504, an estimate of the corrupting data (e.g., extracted corrupting data 306) can be mathematically extracted from the bladder pressure (e.g., measured bladder vesical pressure 210). It should be noted that extracting the estimate of the corrupting data (e.g., corrupting data 304) from the bladder pressure (e.g., measured bladder vesical pressure 210) allows the method 500 to be conducted while requiring only a single sensor located within the patient's bladder. The extracted corrupting data can take the place of a signal that is generally recorded by a second catheter (e.g., placed in the rectum of the patient), allowing the method 500 to proceed with a single sensor located within the patient's bladder.

The corrupting data (e.g., extracted corrupting data 306) can include abdominal pressure data (e.g., extracted abdominal pressure data 308), artifact data (e.g., extracted artifact data 310), and/or any other type of data that may corrupt the detrusor data, each of which can be extracted from the bladder pressure (e.g., measured bladder vesical pressure 210) using one or more mathematical techniques. As an example, the one or more mathematical techniques can include at least one time-invariant technique, at least one time-varying technique, etc., that can be performed on data related to the bladder pressure (e.g., measured bladder pressure 210). The extraction can be executed by a computing device that receives the bladder data (e.g., controller 104). In some instances, the extraction can be done in real-time as the bladder pressure being recorded.

The extraction can be performed using one or more mathematical transforms of at least a portion of data related to the bladder pressure (e.g., bladder vesical pressure 210). The one or more mathematical transforms can include at least one time-invariant extraction technique and/or at least one time-varying extraction technique. In some instances, the extraction includes at least one or more time-varying extraction technique, which may be a non-linear transform and/or a non-time-invariant transform. Examples of the time-varying operation include dynamic time warping approaches, autoregressive modeling such as linear predictive coding, discrete wavelet transform, or the like.

At Step 506, the detrusor pressure (e.g., estimated detrusor pressure 402) of the patient can be estimated (e.g., by the controller 104) based on a difference between the bladder pressure (e.g., measured bladder vesical pressure 210) and the estimate of the corrupting data component (e.g., extracted corrupting data 306). In mathematical terms, detrusor pressure equals bladder pressure minus the estimate of the corrupting data component (e.g., extracted corrupting data 306. At Step 508, an output indicative of the detrusor pressure of the patient based on the estimate of the detrusor pressure data component can be provided (e.g., by the controller 104). It should be noted that if the detrusor pressure is estimated, the remainder of the measured bladder pressure corresponds to the corrupting data component. The corrupting data component can provide an approximation of the abdominal pressure (because the abdominal pressure is the main element of the corrupting data component) that may be important, for example in cases where a patient predominantly uses abdominal pressure to enable bladder voiding. The output can be provided in real time (e.g., as or a few seconds after the bladder pressure is recorded). A diagnosis of the patient can be made (and/or a potential diagnosis eliminated) based on the output.

V. Experimental

This experiment shows the validity of a real-time detrusor pressure estimation system that does not require an abdominal reference sensor. This experiment presents a novel, parameterized framework, which facilitates real time estimation of detrusor pressure from a single pressure sensor in the bladder.

Methods

Data collection: A set of urodynamic data were collected retrospectively from 20 subjects using a standard urodynamic testing protocol. The data was divided into two groups, each containing 10 urodynamic studies. The first group was used for analysis and model development. The second group was used to test predictions of detrusor pressure ($P_{DET}$).

Data analysis: A two-fold analysis process was considered to explore the difference/correlation between bladder vesical pressure ($P_{VES}$) and subtracted calculated $P_{DET}$. At first, the difference between the frequency bands of $P_{VES}$ and calculated $P_{DET}$ were investigated to identify a feasible approach for filtration. Secondarily, wavelet multiresolution analysis was utilized to decompose $P_{DET}$ to find correlation levels between $P_{DET}$ and $P_{VES}$.

Algorithm design: Using the analysis data set, statistical inference was used to extract the basic features of each bladder event. The features included localized statistical mean, median, standard deviation, maximum, zero-crossing rate, and the level of wavelet resolution. An algorithm was developed which included a band-pass filter to remove artifact and noise and a wavelet transformation to extract time-frequency features. To evaluate the effectiveness of the proposed framework, the algorithm was developed using MATLAB® software and tested by processing the data in a frame-wise manner to simulate analysis in real-time with data collection. During this scenario, the test dataset was used to evaluate the performance of the algorithm. The F-score statistical test was utilized to measure algorithm accuracy with the equation: ACC=(TP+TN)/(P+N) where, ACC is accuracy of the algorithm, TP and TN are the true-positive and true-negative detected outliers (coughs and Valsalvas). P and N are the number of overall positive and negative outliers detected by the algorithm since detection and elimination of artifacts is essential to estimate $P_{DET}$ without artifacts or outliers.

Results

The accuracy of detecting cough events in the test dataset (10 UDS) was 99.5%. In contrast, the algorithm detected Valsalva events with an accuracy of only 86.5%. The algorithm detects voiding within 0.5 sec from its start with accuracy of 66.4%.

From the above description, those skilled in the art will perceive improvements, changes, and modifications. Such improvements, changes and modifications are within the skill of one in the art and are intended to be covered by the appended claims.

What is claimed is:

1. A system configured for urological diagnostics of a patient, the system comprising:
 a sensor configured to detect bladder vesical pressure data, wherein the bladder vesical pressure data comprises at least a detrusor pressure data component and a corrupting data component;
 a controller, coupled to the sensor, comprising a processor configured to:
  receive a signal comprising the bladder vesical pressure data from the sensor;
  extract an estimate of the corrupting data component from the bladder vesical pressure data;
  estimate the detrusor pressure data component of the patient based on a difference between the estimate of the corrupting data component and the bladder vesical pressure data; and
  provide an output indicative of a detrusor pressure of the patient based on the estimate of the detrusor pressure data component.

2. The system of claim 1, wherein the estimate of the corrupting data component is extracted based on one or more mathematical transforms of the bladder vesical pressure data.

3. The system of claim 1, wherein the output is provided in real-time with the sensor detecting the bladder vesical pressure data.

4. The system of claim 1, wherein the sensor is within a catheter, wherein the catheter is configured to be inserted in the patient's urethra to the bladder such that the sensor is within the bladder.

5. The system of claim 1, wherein the corrupting data component is extracted by employing at least one time-invariant extraction technique and at least one time-variant extraction technique.

6. The system of claim 5, wherein the bladder vesical pressure data is wavelet transformed and the wavelet transformed bladder vesical pressure data comprises detail coefficients and approximation coefficients,
 wherein the approximation coefficients relate to the detrusor pressure data component and the detail coefficients relate to the corrupting data component.

7. The system of claim 6, wherein the extraction comprises filtering the detail coefficients related to the corrupting data component.

8. The system of claim 1, wherein the processor is further configured to account for a variable relationship between the detrusor pressure data component and the corrupting data component as the bladder empties or fills.

9. The system of claim 1, wherein the corrupting data component comprises abdominal pressure data and/or artifact data.

* * * * *